United States Patent [19]

Calbo, Jr. et al.

[11] Patent Number: 4,922,002

[45] Date of Patent: May 1, 1990

[54] LINEAR, LOW-MOLECULAR-WEIGHT POLYESTER-BASED POLYOL

[75] Inventors: Leonard J. Calbo, Jr., Bethel; Lawrence V. Gallacher, East Norwalk, both of Conn.

[73] Assignee: King Industries, Inc., Norwalk, Conn.

[21] Appl. No.: 355,164

[22] Filed: May 22, 1989

Related U.S. Application Data

[63] Continuation of Ser. No. 684,737, Dec. 21, 1984, Pat. No. 4,888,441, which is a continuation-in-part of Ser. No. 453,222, Dec. 27, 1982.

[51] Int. Cl.$^5$ ............................................. C07C 69/34
[52] U.S. Cl. ..................... 560/193; 524/314; 560/80; 560/84; 560/90; 560/182; 560/198; 560/204
[58] Field of Search ............................... 560/193, 198

[56] References Cited

U.S. PATENT DOCUMENTS

| | | | |
|---|---|---|---|
| 4,000,214 | 12/1976 | Lum et al. ........................ | 525/528 X |
| 4,018,848 | 4/1977 | Khanna ............................ | 527/314 X |
| 4,119,976 | 10/1978 | Anderson et al. ............... | 528/254 X |
| 4,192,826 | 3/1980 | Beresniewicz et al. .......... | 525/425 |
| 4,222,911 | 9/1980 | Christenson et al. ............ | 528/295.5 |
| 4,284,750 | 8/1981 | Amirsakis ........................ | 528/79 |

*Primary Examiner*—Werren B. Lone
*Assistant Examiner*—Vera C. Clarke
*Attorney, Agent, or Firm*—Hedman, Gibson, Costigan & Hoare

[57] ABSTRACT

This invention relates to certain linear, low-molecular-weight polyester-based polyols having at least two hydroxyl groups, low viscosity, high solids content and having the structural formula:

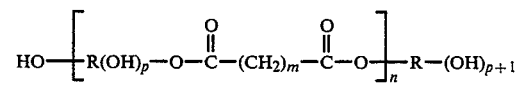

wherein R is a moiety derived from a saturated aliphatic polyhydric alcohol; n is 1 or 2, and at least about 50% by weight, of n is n=1; p is 0 to 4 inclusive and m is 2 to 10 inclusive; said polyol being substantially free of any unreacted polyhydric alcohol.

10 Claims, No Drawings

LINEAR, LOW-MOLECULAR-WEIGHT POLYESTER-BASED POLYOL

This is a continuation of application Ser. No. 06/684,737, filed Dec. 21, 1984, now U.S. Pat. No. 4,888,441, which is a continuation-in-part of Ser. No. 06/453,222, filed on Dec. 27, 1982.

BACKGROUND OF THE INVENTION

This invention is in the field of certain linear, low-molecular-weight polyester-based polyols having at least two hydroxyl groups, comparatively low viscosities and comparatively high solids contents. This invention is also in the field of coating compositions containing these polyols with a cross-linking agent such as aminotriazine compounds and resins such as melamine-formaldehyde resins, urea-formaldehyde resins, epoxy resins, isocyanates or acrylic polymers containing reactive groups, such as hydroxyl groups, carboxyl groups, amide groups, amine groups and the like.

THE PRIOR ART

The instant applicants are aware of the following U.S. Pat. Nos. 4,018,848; 4,119,762; 4,222,911; and British 1,561,076, all of which patents are incorporated herein by reference.

DESCRIPTION OF THE INVENTION

This invention relates to linear, low-molecular-weight, polyester-based polyols having at least two hydroxyl groups, a comparatively low viscosity, and a comparatively high solids content. The invention also relates to a process for the preparation of said polyols. The polyols of the present invention can be prepared by transesterifying a mixture of the alkyl esters of aliphatic dibasic acids, sometimes referred to herein as dicarboxylic acids, or simply esterifying a mixture of said acids with one or more of certain polyhydric alcohols. It is preferred to start with the methyl esters of dicarboxylic acids such as adipic, glutaric and/or succinic acids although other lower alkyl esters could be used, such as the ethyl, propyl and butyl esters and the like, but cost factors generally remove these higher esters from consideration since nothing of value is to be gained by their use. Furthermore, this mixture of methyl esters is available commercially and is therefore additionally preferred, for this reason. These methyl esters, as available commercially, have a mole ratio of about 0.5:1.5:0.6, dimethyl adipate, dimethyl glutarate and dimethyl succinate respectively. Variations of this mole ratio can be tolerated depending upon the desired properties of the final product. Lower viscosities are obtainable with higher levels of glutarate, for example. It is not necessarily limited, for instance, to a mixture of these three recited esters. It is also possible to use mixtures of only two dibasic acid esters or even a single dibasic ester if desired. The same would apply to the dibasic acids and their anhydrides wherever available as well, such as mixtures of the acid compounds or single compounds if desired. The dibasic acids that can be used include succinic, glutaric, adipic, pimelic, suberic, axelaic, sebacic, tartaric and the like including the higher homologs or mixtures thereof. Additionally, one can use tribasic acids such as citric or tricarballylic acid. However, these tribasic acids should be used in combination with the dibasic acids and generally in less than 50 mole percent based on the total moles of acid. Additionally, one can use limited amounts of the aromatic dibasic or tribasic acids whether they are monoaromatic acids such as o-, m-, or p-phthalic acids, mellitic acid and the like including their anhydrides wherever available or their lower alkyl esters or the polyaromatic dibasic acids such as naphthalic acids and the like. When the aromatic acids are used, they must be used with one or more linear aliphatic dicarboxylic acids and in amounts less than the amount of the aliphatic acids. In fact, the aromatic acids, when used, should be present in an amount not exceeding about 30 mole percent based on the total moles of aromatic and aliphatic acids used and preferably not exceeding about 10 mole percent, same basis, for most purposes.

The methyl esters of these dibasic acids, sometimes referred to as dibasic esters, are mixed with one or more polyhydric alcohols containing at least two alcoholic hydroxyl groups of which at least one hydroxyl group is a primary hydroxyl group. The preferred diol is cyclohexane dimethanol, CHDM, for brevity. Examples of other polyhydric alcohols with primary hydroxyls that could be used include neopentyl glycol; 1,4-butanediol; 1,6-hexanediol; 2,2,4-trimethyl 1,3 pentanediol; 1,2,6-hexanetriol; trimethylol ethane; trimethylol propane; pentaerythritol, dipentaerythritol, sorbitol, mannitol; dimethylolpropionic acid; and 2,2-dimethyl-3-hydroxypropyl-2,2-dimethyl-3-hydroxypropionate and the like. Diols containing a mixture of primary and secondary hydroxyls may be used, and include propylene glycol and 1,2-hexylene glycol. Mixtures of other diols may also be used.

Usually a catalyst is employed for the esterification/transesterification reaction for the purpose of lowering reaction temperatures and reducing color development in the product. Typical catalysts that may be employed are the alkoxides of titanium, soluble tin compounds such as dibutyl tin dilaurate and soluble manganese compounds such as $Mn(OAc)_2$. Catalyst levels of 0.005 to 1.0% by weight of the reactants can be used or typical levels of 0.01 to 0.5% on the same basis can be used.

In the preferred embodiment, the mixed methyl esters are combined with CHDM in a suitable reaction vessel and heated in the presence of a conventional transesterification catalyst, such as a titanium alkoxide, in order to accomplish transesterification. The methanol is split off during the heating step and is easily removed as free methanol until the new reaction product is devoid of or substantially completely free of methanol. The resultant product will contain, as a general rule, some varying amounts of unreacted cyclohexane dimethanol depending on the initial mole ratio of the reactants. The initial starting mole ratios of the dimethyl esters, also referred to as dibasic esters, considered as a whole and as one entity, to the cyclohexane dimethanol can be varied between about 1.0:1.5 and 1.0:10.0 respectively, dimethyl esters to CHDM, but preferably between about 1.0:2.0 and 1.0:4.0 respectively, dimethyl esters to CHDM.

The ultimately produced polyol will be devoid of or substantially completely free of any cyclohexane dimethanol. The expressions, devoid of or substantially completely free of, means less than about 12% and preferably less than about 4% by weight based on the total weight of the final polyol reaction product.

The conventional technique used to remove the unreacted diol is batch distillation. The preferred technique uses continuous rapid stripping of the CHDM or other alcoholic reactant, immediately followed by cooling the product to prevent chemical reaction and equilibration. Continuous large-scale rapid stripping can be accomplished using several processes including continuous column distillation, shell-and-tube evaporators and falling-film evaporator-strippers, to name several examples. It is conceivable that other techniques could be applied to remove excess diol, including liquid-liquid extraction or crystallization.

A useful laboratory technique to demonstrate the importance of rapid stripping and immediate cooling utilizes a rotary evaporator and an oil bath. The charge is a mole ratio of 1:3, dibasic acid to cyclohexane dimethanol transesterification product into the rotary evaporator at an absolute pressure of 1-2 Torr and an oil bath temperature of 180°-185° C. for eight minutes. 43% of the charge is volatilized and the resultant product has a viscosity of 13,800 cps, at 25° and a 60 minutes solids content of 98.8%.

If one were to use the batch distillation technique, one experiences high viscosity and low solids content. The reason for these adverse results may reside in the fact that the product is equilibrating chemically toward the most probable component distribution during the slow batch distillation. Actually, polyesterification reactions and transesterification reactions such as this always lead to equilibrium product distributions dictated by simple statistical considerations. Therefore, a batch distillation of a high glycol-to-acid polyol to a lower glycol/acid mole ratio may tend to give the same equilibrium product one would obtain by running the whole transesterification reaction at the final mole ratio.

The expression, "Low Viscosity", as used hereinabove and as applied to the products of the present invention, means viscosities of not more than about 15,000 cps and preferably not more than about 10,000 cps when measured on a substantially 100% solids material at 25° C. However, when aromatic polycarboxylic acids are used as one of the acidic compounds, these viscosities will be higher, such as 30,000 cps or even higher. The viscosities are, in fact, low when compared with the viscosities of similar polyols that are prepared by processes that are outside of the scope of the process of the present invention even though these similar polyols contain substantially the same reactants and contain substantially the same amounts of each reactant on a mole/mole basis.

Although one of the principal uses of the polyols of the present invention is in coating compositions, one may use these polyols in such areas as adhesives, foams, moldings, elastomers, and laminates with whatever modifications may be required and such further additives as fillers, layers, and the like.

Surprisingly, it was found that rapid stripping of a 3:1 mole ratio CHDM:dibasic ester polyester polyol feed followed by rapid cooling removed approximately 35% of the total weight of feed as CHDM and gave products which combined both low viscosity, on the order of 10,000 cps at 25° C., and high solids content, on the order of 98%. In contrast, conventional batch distillation removing the same weight of CHDM with or without rapid-cooling gives products with much higher viscosities, on the order of 19,000 cps or higher at 25° C., and lower solids content, on the order of 90%. These properties are extremely important in the formulation, application, and performance of high-solids coatings, as will be shown elsewhere in this application.

In principle, the same technique is applicable to other ester polyols as well. The maximum positive effect is achievable when all of the reactive groups have equal chemical reactivity. Thus, a diol with one primary and one secondary hydroxyl group will naturally yield a diester high in secondary hydroxyls, because the primaries will have reacted first to form the diester. Further, it will be much harder to get chain extension once one has diester, since the secondary hydroxyl end groups are not very reactive. In a case like this, one would be able to get a good yield of diester starting with a low diol:acid ratio, not much over 2:1. Following the same line of reasoning, one should be able to remove excess diol molecules easily without significant chain extension, so it should be possible to get extremely high solids.

In one embodiment, a wiped-film evaporator is used to accomplish the rapid stripping of the CHDM.

A wiped-film evaporator, such as the Artisan Rototherm ® thin-film evaporator consists of a heated cylindrical chamber with a feed inlet at the top above a rotatable heated cylindrical member or rotor onto which the feed flows, maintaining the feed as a thin film on the inner wall of the cylindrical chamber. A top exit is provided for the CHDM vapor to escape. An outlet is provided at the bottom from which the desired polyol product emerges. The rotor is attached to an electric motor which provides the rotation. The temperature of the heated film is about 350° F. and the absolute pressure is about 2 mm. The residence time of the material being treated varies from about 30 seconds to 2 minutes. The product leaving at the outlet passes through a heat-exchanger which cools it to approximately 200° F. before it flows into the product storage vessel.

The polyols of the present invention can be used as coating compositions without modification when combined with any one or more of a host of crosslinking agents, such as polyisocyanate or the aminotriazinealdehyde such as the melamine-formaldehyde resins and the like. One can also use the acrylic co-polymers containing alcoholic hydroxy groups in conjunction with the polyols of the present invention and crosslinking agents with or without other reactive groups such as carboxy groups, amide groups, amine groups and the like as shown in the U.S. Pat. Nos. 3,663,389, 3,894,993, and 3,945,961. These patents are incorporated herein by reference.

Other conventional additives may also be used such as pigments, catalysts, and the like.

In order that the concept of the present invention may be more completely understood, the following examples are set forth in which all parts are parts by weight unless otherwise indicated. These examples are set forth primarily for the purpose of illustration and any specific enumeration of detail contained herein should not be interpreted as a limitation on the case except as is indicated in the appended claims.

EXAMPLE 1

Into a suitable glass reactor, the following ingredients were charged:
 98.27 parts CHDM (309.6 moles)
 7.37 parts Dibasic esters (20.9 moles)
Using a mantle, the contents of the reactor were heated to 125° C. with agitation, and then 12.3 parts of titanium tetrabutoxide were added. Heating was continued while a nitrogen flow of 100 ml/min. into the reactor was maintained. When the temperature reached 160° C., the temperature was maintained at that level, and 29 parts of dibasic esters (82.2 moles) were then metered into the reactor over a 3 hour period with continuous agitation. During the dibasic esters addition period, methanol vapor was evolved continuously and condensed with a water-cooled glass condenser to recover 7.4 parts of liquid methanol.

This product was then processed in a 1 square foot Artisan Rototherm wiped-film evaporator. The feed rate was set at 19 ml per minute with a product outlet temperature of 175° C. at a pressure of approximately 1 torr. The product was passed through a cooled outlet pipe to adjust the final product temperature to 95° C. The finished product had a viscosity of 9000 cps at 25° C. and showed 98% solids content in a one hour test.

The following examples are illustrative of the utility of the present invention:

EXAMPLE 2

A coating composition is prepared by mixing the following ingredients:

| Formulation | Parts |
| --- | --- |
| Polyol from Example 1 | 60 |
| Hexakis (methoxymethyl) melamine[1] | 40 |
| n-Butanol | 10 |
| Flow control agent[2] | 0.4 |
| Acid catalyst[3] | 2 |
| % Solids = 89.5 | |
| Viscosity = 880 cps | |

[1]Cymel 303, American Cyanamid Company
[2]3M Co. (a fluorocarbon)
[3]King Industires, Inc. - DNNDSA The coating is applied by draw down bar to yield approximately 1 mil film thickness on a phosphate treated steel panel which is then placed in a forced draft convection oven and cured under the following several conditions of varying time and temperature:

| Time, min. | 20 | 15 | 10 | 5 |
| --- | --- | --- | --- | --- |
| Temp, °F. | 200 | 225 | 250 | 275 |
| Pencil Hardness | H-2H | H-2H | H-2H | H-2H |
| Double MEK Rubs | 100 | 100 | 100 | 100 |
| Reverse Impact, in. lb. | 80+ | 80+ | 80+ | 80 |

EXAMPLE 3

The following example illustrates the improved coating properties that result when a polyol of the present invention is used as a minor component of the binder system.

The ingredients listed below are blended in a suitable container.

| Formulation | 1 | 2 | 3 |
| --- | --- | --- | --- |
| Acrylic Resin[1] | 200 | 280 | 240 |
| Hexakis(methoxymethyl) melamine[2] | 25 | 50 | 60 |
| Polyol of Example | — | 10 | 20 |
| Isopropanol | 25 | 42 | 44 |
| Xylene | — | 18 | 36 |
| DNNDSA[3] Amine Blocked Catalyst | 2.5 | 4.0 | 4.0 |
| Acrylic/Melamine/Polyol Wt. Ratio | 80/20/— | 70/25/5 | 60/30/10 |

[1]Rohm & Haas Co.
[2]Cymel 303, American Cyanamid Co.
[3]King Industries, Inc.

The coating mix is applied by draw down bar to iron phosphated cold rolled steel and cured for 20 min. at 150° C. in a forced draft convection oven. The properties are set forth hereinbelow.

| | 1 | 2 | 3 |
| --- | --- | --- | --- |
| Pencil Hardness | 2-3H | 4-5H | 2-3H |
| Double MEK Rubs | 100+ | 100+ | 100+ |
| Adhesion Loss, % | 0 | 0 | 0 |
| Impact, | | | |
| reverse | 30-40 | 80+ | 80+ |
| direct | 80+ | 80+ | 70/80 |
| Water Immersion 250 hr, 50° C. Blister Rating | Few 8 | Very Few 8 | Very Few 8 |

EXAMPLE 4

In this example a pigmented enamel is prepared by grinding titanium dioxide in a polyol of the present invention. The enamel thus prepared has very high solids and excellent low temperature cure properties as illustrated herein below.

| Mix in a suitable container: | |
| --- | --- |
| Titanium dioxide | 550 parts |
| Polyol of Example 1 | 250 |
| n-Butanol | 75 |
| Cellosolve Acetate | 125 |
| Disperse on Cowles Dissolver | |
| Let Down | |
| Acrylic Resin[1] | 333 |
| Hexakis(methoxymethyl)melamine[2] | 200 |
| n-Butanol | 30 |
| % Solids, wt | 80 |
| Viscosity, cps | 440 |
| Polyol/Acrylic/Melamine Wt. Ratio | 50/50/40 |

| Film Properties White Enamel | | | |
| --- | --- | --- | --- |
| Cure: | | | |
| Time, min. | 15 | 15 | 30 |
| Temp., °C. | 121 | 93 | 82 |
| Catalyst: DNNDSA, % TRS | 0.6 | 2.0 | 2.75 |
| Pencil Hardness | 2-3H | H-2H | H-2H |
| MEK Rubs | 200 | 200 | 170 |
| Reverse Impact | 80+ | 80+ | 80+ |
| Gloss, 60° | 89 | 91 | 91 |
| Water Immersion 250 hr., 50° C. Gloss, 60° | 89 | 90 | 86 |

TRS = Total Resin Solids
[1]King Industries, Inc.
[2]Cymel 303, American Cyanamid Co.

EXAMPLE 5

A room temperature curing coating composition is prepared by mixing the polyol of Example 1 with an isocyanate crosslinking agent in the manner described below.

| Components | Parts |
| --- | --- |
| Polyol of Example 1 | 100 |
| Polyisocyanate[1] | 82 |
| Xylene | 30 |
| 2-Ethoxyethyl Acetate | 30 |
| % Solids = 75 | |
| Viscosity = 60 sec. Ford 4 Cup | |

[1]Mobay Chemical Corp.

The coating may be either sprayed or applied by draw down bar to a steel panel with the resultant film properties.

| After 24 hr. aging of the coated panel at room temperature: | |
|---|---|
| Pencil Hardness | 5-6H |
| MEK Rubs | 200 |
| Impact. | |
| reverse | 160 in. lb. |
| direct | 160 in. lb. |

Coating is tack-free after 6 hours.

EXAMPLE 6

The following ingredients were charged into a suitable glass reaction vessel:
270.4 parts 1,4-Butanediol (3.0 moles)
160.0 parts Dibasic Esters (1.0 mole)

Using a heating mantle and agitator the contents of the flask were heated to 125° C., and then 1.77 parts of titanium tetrabutoxide were added. Heating was continued, and at 137° C. methanol began distilling over and was recovered continuously with a water-cooled total condenser. Three hours and twenty minutes after the start of the experiment, the temperature was 176° C. and the evolution of methanol appeared to be over, with 54 parts of condensate collected.

The intermediate product at this point was checked for solids content using a modified ASTM D-2369-81-B procedure: Obtain the tare weight "T" of a 58 mm aluminum weighing dish containing a paper clip and record to the nearest 0.1 mg. Add 0.5±0.1 g of sample using a syringe and record sample weight "S" to nearest 0.1 mg. Add 2±0.2 g of toluene, mix contents with paper clip until homogeneous, and finally place paper clip in dish. Heat the dish and contents in a forced draft oven for 60 minutes at 110° C. Cool in a desiccator to ambient temperature and weight dish and contents to nearest 0.1 mg (weight "F"). Determine percent solids as follows and report to nearest 0.1%:

$$\% \text{ Solids} = \frac{100 \times (F - T)}{S}$$

The solids content was found to be 68.9% using this test. This test is and has been used to determine solids content throughout this specification.

The intermediate product was then stripped on a rotary evaporator for 10 minutes at 201° C. and 2.5 torr and quickly cooled to room temperature. The final product so produced had 98.3% solids following the above test procedure, and a viscosity of 4500 cps at 25° C.

EXAMPLE 7

This example illustrates the use of a trihydric alcohol to prepare the product of this invention.

The following ingredients were charged into a suitable glass reaction vessel set up with a heating mantle, stirrer, total condenser, and thermometer:
275.7 parts 1,2,6-Hexanetriol (2.055 moles)
109.6 parts Dibasic Esters (0.685 mole)

The mantle was then used to heat the contents of the flask while agitating. At 122° C. batch temperature, 1.58 parts of titanium tetrabutoxide was added, and heating was continued. Methanol began distilling over at 170° C. The reaction was over in 2 hours, reaching a peak temperature of 224° C. and generating 46 parts of distillate.

The intermediate product had a solids content of 95%. After stripping in a rotary evaporator at 250° C. and 1.6 torr, the resulting product showed a solids content of 100% and a viscosity of 11,500 cps at 25° C.

EXAMPLE 8

This example shows the use of neopentyl glycol and dibasic esters to prepare the product of this invention.

To a suitable stainless steel reactor was charged 409 parts of dibasic ester. The agitator was started and then 400 parts of neopentyl glycol were charged.

Steam heat was then applied to the jacket to raise the contents of the reactor to 140° F. to dissolve the neopentyl glycol. Then an additional 400 parts of neopentyl glycol was added and heating was continued. When the batch temperature reached 200° F., 3 parts of dibutyltin dilaurate were added.

Heating was continued with agitation. Methanol began distilling over at 300° F. After an additional 3 hours, the temperature had risen to 335° F. and methanol evolution stopped. At this point 151 parts of condensed methanol had been collected. The batch temperature was maintained at 325°-335° F. for an additional hour under a nitrogen sweep of 10 scfm. The batch was then cooled to 200° F. and drummed prior to stripping.

Evaluation of this intermediate product showed a 65% solids content when tested in accordance with the procedure of Example 6. The material was stripped using a wiped-film evaporator with a preevaporator stage and rapid product quenching. A maximum temperature of 365° F. at 150 torr produced a final product with a measured solids content of 96.0% and a viscosity of 3720 cps at 25° C.

In the polyols of the present invention, the amount of the bracketed moiety, where n is 1 or 2, is at least about 50% by weight of n=1 and m is 2 to 10 inclusive. It is preferred that such moiety is sufficient to provide an average molecular weight of between about 300 and 600 and preferably between about 350 and 500. The final reacted mole ratio of the dibasic acid to the polyhydric alcohol is between about 1.0:1.3 and 1.0:2.4 respectively and preferably between about 1.0:1.5 and 1.0:2.1 respectively.

The process of the present invention requires a stripping temperature of from about 150° C. to 225° C. at an absolute pressure of from about 0.05 to 200 torr for a period of time from about 10 seconds to 10 minutes.

It is preferred to use a temperature from about 160° C. to 210° C. at an absolute pressure of from about 0.1 to 150 torr for a period of time from about 20 seconds to about 2 minutes.

We claim:
1. A linear, low-molecular-weight polyester-based polyol having at least two hydroxyl groups, low viscosity, high solids content and having the structural formula:

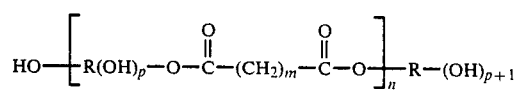

wherein R is a moiety derived from saturated aliphatic polyhydric alcohol; n is 1 or 2, and at least about 50% by weight of n is n=1; p is 0 to 4 inclusive and m is 2 to 10 inclusive; said polyol being substantially free of any unreacted polyhydric alcohol.

2. A polyol according to claim 1 in which the moiety R is derived from cyclohexane dimethanol.

3. A polyol according to claim 1 in which the mole ratio of the dibasic acid to the polyhydric alcohol is between about 1.0:1.3 and about 1.0:2.4 respectively.

4. A polyol according to claim 1 in which the mole ratio of the dibasic acid to the polyhydric alcohol is between about 1.0:1.5 and 1.0:2.1 respectively.

5. The polyol according to claim 1 in which the average molecular weight of said polyol is between about 300 and 600.

6. The polyol according to claim 3 in which the polyhydric alcohol is cyclohexane dimethanol.

7. The polyol according to claim 1 in which $m=2$ to 4 inclusive.

8. The polyol according to claim 7 in which the mole ratio of the dibasic acid to the polyhydric alcohol is between about 1.0:1.3 and 1.0:2.4 respectively.

9. The polyol according to claim 7 in which the average molecular weight of said polyol is between about 300 and 600.

10. The polyol according to claim 7 in which the mole ratio of the dibasic acid to the polyhydric alcohol is between about 1.0:1.5 and 1.0:2.1 respectively.

* * * * *